United States Patent
Jiang et al.

(10) Patent No.: US 12,055,273 B2
(45) Date of Patent: Aug. 6, 2024

(54) SYSTEM AND METHOD FOR SUPPLYING ACETYLENE TO AN APPARATUS USING ACETYLENE

(71) Applicant: L'Air Liquide, Société Anonyme pour l'Etude et l'Exploitation des Procédés Georges Claude, Paris (FR)

(72) Inventors: Zhijun Jiang, Shanghai (CN); Qingqing Zhu, Shanghai (CN)

(73) Assignee: L'Air Liquide, Societe Anonyme Pour l'Etude et l'Exploitation des Procedes, Georges Claude Paris (FR)

( * ) Notice: Subject to any disclaimer, the term of this patent is extended or adjusted under 35 U.S.C. 154(b) by 127 days.

(21) Appl. No.: 17/954,466

(22) Filed: Sep. 28, 2022

(65) Prior Publication Data
US 2023/0094475 A1 Mar. 30, 2023

(30) Foreign Application Priority Data

Sep. 28, 2021 (CN) .......................... 202111143827.4

(51) Int. Cl.
*F17C 7/00* (2006.01)
*F17C 13/02* (2006.01)
(Continued)

(52) U.S. Cl.
CPC ................ *F17C 7/00* (2013.01); *F17C 13/02* (2013.01); *F17C 13/045* (2013.01); *F17D 1/04* (2013.01); *F17D 3/01* (2013.01); *G01N 30/66* (2013.01); *G01N 30/68* (2013.01); *G05D 16/2033* (2013.01); *F17C 2205/0338* (2013.01); *F17C 2205/0352* (2013.01);
(Continued)

(58) Field of Classification Search
CPC .......... F17C 7/00; F17C 13/02; F17C 13/045; F17C 2205/0338; F17C 2205/0352; F17C 2221/018; F17C 2227/041; F17C 2250/032; F17C 2250/0452; F17C 2250/0689; F17D 1/04; F17D 3/01; G01N 30/66; G01N 30/68; G01N 2030/743; G05D 16/2033
USPC ........................................................... 141/1
See application file for complete search history.

(56) References Cited

U.S. PATENT DOCUMENTS

| | | | |
|---|---|---|---|
| 4,863,493 | A | 9/1989 | Kotani et al. |
| 6,124,517 | A | 9/2000 | Kaminsky et al. |

(Continued)

FOREIGN PATENT DOCUMENTS

| | | |
|---|---|---|
| CN | 110410662 A | 11/2019 |
| CN | 112097099 A | 12/2020 |
| JP | 2008 107127 | 5/2008 |

*Primary Examiner* — Timothy P. Kelly
*Assistant Examiner* — Christopher M Afful
(74) *Attorney, Agent, or Firm* — Elwood L. Haynes

(57) ABSTRACT

Disclosed in the present invention is a system and method for supplying acetylene to an apparatus using acetylene, the system having at least one acetylene storage apparatus and an acetylene content analysis apparatus. The system and method disclosed in the present invention can utilize the capacity of an acetylene cylinder to a higher degree; before the solvent impurity concentration in acetylene gas reaches a level where it is no longer suitable, a more accurate understanding of the usable acetylene amount in the acetylene storage apparatus can be gained through detection, thereby reducing the number of times that the acetylene storage apparatus is refilled and replaced, and lowering the user's total costs.

8 Claims, 1 Drawing Sheet

(51) Int. Cl.
 *F17C 13/04* (2006.01)
 *F17D 1/04* (2006.01)
 *F17D 3/01* (2006.01)
 *G01N 30/66* (2006.01)
 *G01N 30/68* (2006.01)
 *G01N 30/74* (2006.01)
 *G05D 16/20* (2006.01)

(52) U.S. Cl.
 CPC .. *F17C 2221/018* (2013.01); *F17C 2227/041* (2013.01); *F17C 2250/032* (2013.01); *F17C 2250/0452* (2013.01); *F17C 2250/0689* (2013.01); *G01N 2030/743* (2013.01)

(56) References Cited

U.S. PATENT DOCUMENTS

| | | | |
|---|---|---|---|
| 6,314,981 B1 | 11/2001 | Mayzou et al. | |
| 2004/0262222 A1* | 12/2004 | Chordia | G01N 30/82 436/178 |
| 2008/0053908 A1* | 3/2008 | Chordia | B01D 15/20 210/85 |
| 2008/0242912 A1 | 10/2008 | Letessier et al. | |
| 2010/0069689 A1* | 3/2010 | Maykut | C07C 7/09 585/16 |
| 2017/0185093 A1 | 6/2017 | Isom et al. | |

* cited by examiner

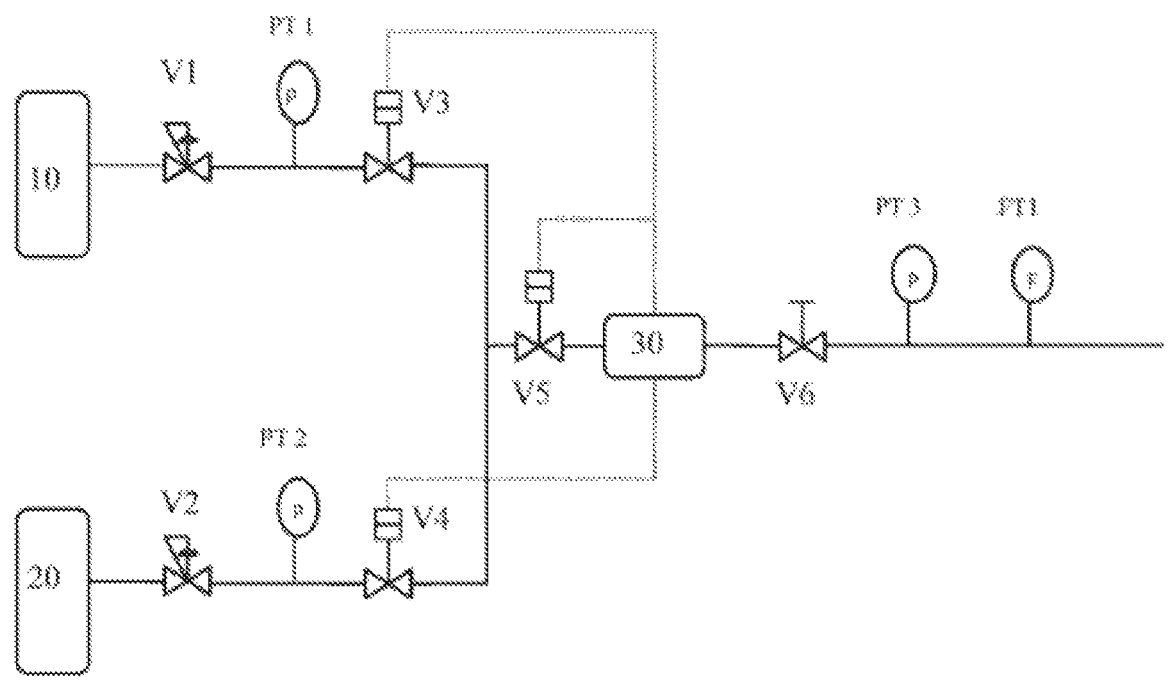

SYSTEM AND METHOD FOR SUPPLYING ACETYLENE TO AN APPARATUS USING ACETYLENE

CROSS REFERENCE TO RELATED APPLICATIONS

This application claims the benefit of priority under 35 U.S.C. § 119 (a) and (b) to Chinese Patent Application No. 202111143827.4, filed Sep. 28, 2021, the entire contents of which are incorporated herein by reference.

TECHNICAL FIELD

The present invention relates to the field of component determination and relates to a system and method for supplying acetylene to an apparatus using acetylene, in particular to a system and method for supplying a steady, continuous acetylene stream with a controllable solvent content.

BACKGROUND ART

Acetylene is often used as a source material for depositing carbon and carbon-containing films in semiconductor applications. Acetylene is a highly flammable gas; contents in air of 2%-80% lie in the range of flammability. To securely store this highly dangerous gas, acetylene will generally be dissolved in an organic solvent, such as acetone, dimethylformamide (DMF) or N-methylpyrrolidone. The interior of a cylinder needs to be filled with porous material with a porosity of about 90% to absorb the organic solvent uniformly, and this can prevent and avoid decomposition of acetylene gas, avoiding the development of voids which would allow the accumulation of free acetylene in an oxidized state. Although cylinders of dissolved acetylene of this kind can solve the safety problem of acetylene gas, acetone has a boiling point of just 56.53° C. and so volatilizes very easily. As the acetylene is gradually consumed, the proportion of acetone mixed into the acetylene gas released from the cylinder will increase considerably, and this is highly likely to have a major impact on the technical process and/or final product quality, or cause fluctuation therein.

To guarantee a supply of acetylene at a steady flow rate, the user needs to estimate the pressure of acetylene gas remaining in the cylinder, in order to promptly switch to a new acetylene cylinder, and thereby effectively limit the concentration of solvent in the acetylene gas. For an acetone-acetylene cylinder, the empirical value of the switching pressure is about 5-6 bar; for a DMF-acetylene cylinder, the empirical value of the switching pressure is about 3.5 bar. However, the amounts of dissolved solvents contained in different acetylene cylinders vary and are affected by different operating conditions, and solvent volatilization speeds also vary; therefore, the abovementioned method of estimating the pressure of remaining acetylene gas is not precise enough, and is unable to directly indicate the acetylene content in a cylinder. If a preset value of remaining acetylene gas pressure is too low, a large amount of solvent will still inevitably be introduced in the technical process, and this is undesirable; if the preset value of remaining acetylene gas pressure is too high, frequent switching of cylinders will be very uneconomical.

In view of the above, the question of how to design a new system and method for supplying acetylene, in order to precisely indicate the purity or content of acetylene in a cylinder, to eliminate the abovementioned deficiencies and shortcomings in the prior art, is an issue in urgent need of a solution from those skilled in the art.

SUMMARY OF THE INVENTION

To overcome the abovementioned technical problem, the present invention provides a system and method for supplying acetylene to an apparatus using acetylene, wherein the supplied acetylene can maintain a stable and uninterrupted supply concentration.

To achieve the above object of the invention, a first aspect of the present invention discloses a system for supplying acetylene to an apparatus using acetylene, the system comprising:

at least one acetylene storage apparatus, for supplying a feedstock comprising acetylene and a solvent to the apparatus using acetylene; and an acetylene content analysis apparatus, comprising an analytical instrument and a data processing component;

wherein the analytical instrument comprises gas chromatography with a thermal conductivity detector or a flame ionization detector or Fourier-transform infrared spectroscopy, and is used to detect a solvent concentration in the feedstock;

the data processing component is configured to analyse the solvent concentration from the analytical instrument as time passes, compare it with a preset value of solvent concentration, and output a control result.

Furthermore, the system further comprises a data transmission module, for transmitting the solvent concentration from the analytical instrument to the data processing component.

Furthermore, the data processing component is a computer, a mobile device, or a logic controller with a microprocessor.

Furthermore, the solvent is selected from acetone, dimethylformamide, N-methylpyrrolidone, or a combination thereof.

Furthermore, the preset value of solvent concentration is 10000 ppm or less solvent contained in acetylene.

Furthermore, at least one pressure regulating valve is provided upstream of the apparatus using acetylene, for controlling the switching of each acetylene storage apparatus.

Furthermore, the control result comprises the opening/closing of each pressure regulating valve.

Furthermore, each acetylene storage apparatus outputs acetylene through a respective branch, and a control valve is further provided on each branch, for controlling each branch to deliver the feedstock to the acetylene content analysis apparatus.

Furthermore, the acetylene storage apparatus comprises a first acetylene storage apparatus and a second acetylene storage apparatus, and when the analytical instrument detects that the solvent concentration in an acetylene stream outputted by the first acetylene storage apparatus is higher than the preset value, a switch takes place to the second acetylene storage apparatus.

A second aspect of the present invention is a method for supplying acetylene to an apparatus using acetylene, the method comprising the steps of:

(1) providing at least one acetylene storage apparatus, for supplying a feedstock comprising acetylene and a solvent to the apparatus using acetylene;

(2) arranging an acetylene content analysis apparatus, a pressure regulating valve and a control valve upstream of the apparatus using acetylene, the acetylene content analysis apparatus comprising an analytical instrument and a data processing component, the pressure regulating valve being used to control switching of each acetylene storage apparatus, and the control valve being used to control the delivery of the feedstock to the acetylene content analysis apparatus;

(3) the analytical instrument detecting a solvent concentration in the feedstock and transmitting same to the data processing component, and the data processing component controlling the pressure regulating valve, to switch each acetylene storage apparatus.

Compared with the prior art, the technical solution provided in the present invention has the following advantages:

The system and method disclosed in the present invention can utilize the effective amount of acetylene in an acetylene cylinder to a higher degree; before the amount of solvent reaches a level where it is no longer suitable, a more accurate understanding of the usable capacity of the acetylene cylinder can be gained through detection, thereby reducing the number of times that the cylinder is refilled and replaced, and lowering the user's total costs.

BRIEF DESCRIPTION OF THE FIGURES

Further understanding of the advantages and spirit of the present invention can be gained through the following detailed description of the invention and accompanying drawings.

FIG. 1 is a schematic flow chart of a system for supplying acetylene in an embodiment of the present invention.

DETAILED DESCRIPTION OF THE INVENTION

Specific embodiments of the present invention are explained in detail below in conjunction with the accompanying drawings. However, the present invention should be understood to not be limited to embodiments such as those described below, and the technical concept of the present invention may be implemented in combination with other well-known technologies or other technologies having the same function as those well-known technologies.

In the explanation of particular embodiments below, in order to clearly demonstrate the structure and manner of operation of the present invention, many directional words will be used for description, but words such as "front", "rear", "left", "right", "outer", "inner", "outward", "inward", "axial" and "radial" should be understood as being terms of convenience rather than defining words.

In the explanation of particular embodiments below, it must be understood that orientational or positional relationships indicated by terms such as "length", "width", "up", "down", "front", "rear", "left", "right", "vertical", "horizontal", "top", "bottom", "inner" and "outer" are based on the orientational or positional relationships shown in the drawings, and are merely intended to facilitate and simplify the description of the present invention, without indicating or implying that the apparatus or element referred to must have a specific orientation or be constructed and operated in a specific orientation, and therefore should not be understood as limiting the present invention.

In addition, the terms "first" and "second" are only used for descriptive purposes, without limiting chronological order, quantity, or importance, and, rather than being construed as indicating or implying relative importance or implicitly pointing out a quantity of the indicated technical feature, are only intended to differentiate one technical feature from another technical feature of the present technical solution. Thus, features for which "first" and "second" are defined may explicitly or implicitly include one or more of said feature. In the description of the present invention, the meaning of "multiple" is two or more, unless clearly and specifically specified otherwise. Similarly, qualifiers similar to "a" appearing herein do not indicate a definition of quantity, but describe a technical feature that has not appeared in the preceding text. Similarly, unless modified by a specific quantity measure word, nouns herein should be regarded as including both singular and plural forms, i.e. the technical solution may include a single one of the technical feature concerned, but may also include a plurality of the technical feature. Similarly, modifiers similar to "approximately" and "about" appearing before numerals herein usually include the numeral, and the specific meaning should be understood in light of the context.

It should be understood that in the present application, "at least one (item)" means one or more, and "multiple" means two or more. The expression "and/or" is used to describe the associative relationship between associated objects, and indicates that three types of relationship may exist; for example, "A and/or B" can mean three situations, namely that A alone is present, B alone is present, and A and B are both present, wherein A and B may be singular or plural. The symbol "/" generally means that the preceding and following associated objects have an "or" relationship. The expression "at least one of the following (items)" or similar means any combination of these items, including a single (item) or any combination of multiple (items). For example, at least one (item) of a, b or c can mean a, b, c, "a and b", "a and c", "b and c", or "a and b and c", wherein a, b and c may be single or multiple.

In the present invention, unless otherwise explicitly stipulated and defined, terms such as "mounted", "connected to each other", "connected" and "fixed" should be understood in a broad sense. For example, there may be a fixed connection, or there may be a removable connection, or the connection may be integral; there may be a mechanical connection, or there may be an electrical connection; there may be a direct connection, or there may be an indirect connection via an intermediate medium, there may be internal communication between two elements or an interactive relationship between two elements. Those skilled in the art can understand the specific meaning of the above terms in the present invention according to the specific circumstances. The expression "fixedly connected" or "fixed connection" or "non-movably connected" is understood to mean that a connection between two or more structural members is not configured to provide relative movement. An example of a fixed connection is a welded joint or a bolt connection, and in some cases a weld seam and bolt connection. The expression "movably connected" or "movable" or "movable connection" is understood to mean that a connection between two or more structural members allows horizontal and/or vertical relative movement between the members under extreme driving force loads. Such a connection generally does not allow movement under static loads or ordinary driving force loads (e.g. such as are exerted from light/medium wind forces).

The terms "unit", "member", "object" and "module" described herein indicate units used to process at least one function and operation, and can be implemented by means of hardware components or software components and combinations thereof.

The terms "sealed connection" or "sealable connection" indicate the following characteristics: two component containers are connected by welding, connected by bonding, connected or connectable by threads or in another way, such that when pressure is established to empty a multi-chamber mixed container, there will be no leakage of contents from the multi-chamber mixed container through the sealed connection.

As used herein, the expression "containing almost no solvent" means containing 300 ppm or less solvent, preferably containing 200 ppm or less solvent, more preferably containing 100 ppm or less solvent, and most preferably containing 80 ppm or less solvent.

As used herein, a "pressure regulating valve" has the functions of flow rate control and maintaining a certain pressure difference, and is positioned in a pipeline between an acetylene cylinder and an apparatus using acetylene.

Unless clearly indicated otherwise, each aspect or embodiment defined here can be combined with any other aspect(s) or embodiment(s). In particular, any preferred or advantageous feature indicated can be combined with any other preferred or advantageous feature indicated.

Specific embodiments of the present invention are explained in detail below with reference to FIG. 1.

The system for supplying acetylene provided in this embodiment supplies a stable, compliant and uninterrupted acetylene delivery to an apparatus using acetylene in a subsequent process by monitoring in real time a solvent concentration in an acetylene stream from an acetylene storage apparatus. The system comprises two acetylene cylinders or two sets of multiple acetylene cylinders as the acetylene storage apparatus. Based on the result of real-time monitoring of the solvent concentration in the outflow streams of each acetylene cylinder, more precise automatic switching between each acetylene cylinder is achieved.

For example, when used for a low-pressure carburization process, remote control and switching between the acetylene cylinders depends on the solvent concentration in the acetylene stream, ensuring that each acetylene cylinder can output an acetylene stream continuously and steadily, thus saving extra maintenance time in a subsequent process. In this way, cost-effectiveness is achieved through optimized utilization of the capacity of the acetylene cylinders.

The system comprises one or more analytical instruments for detecting acetylene and solvent concentrations; examples of such analytical instruments may be gas chromatography with a thermal conductivity detector (TCD) or a flame ionization detector (FID) or Fourier-transform infrared spectroscopy (FTIR). The system further comprises a data transmission module, for transmitting the solvent concentration from the analytical instrument to a data processing component, and outputting a control result, thereby controlling the opening/closing of each pressure regulating valve. The data transmission module may be a Wi-Fi network.

Each acetylene cylinder may be controlled independently by a separate pressure regulating valve.

The data processing component may be a computer, a mobile device, or a logic controller with a microprocessor; the present invention does not impose restrictions in this respect.

Taking as an example the case where the system comprises two acetylene cylinders 10 and 20: on condition that process requirements are met, acetylene cylinder 10 is designed to steadily and uninterrupted supply acetylene with a solvent concentration meeting requirements to the apparatus using acetylene, while acetylene cylinder 20 can act as a backup.

When the solvent concentration in the acetylene stream of acetylene cylinder 10 monitored by the analytical instrument reaches a preset value, a pressure regulating valve is opened to automatically output an acetylene stream from acetylene cylinder 20. Thereafter, a process gas stream flowing to a low-pressure carburization (or vacuum carburization) process will not be interrupted, because an operator will be able to replace acetylene cylinder 10 while acetylene cylinder 20 supplies acetylene to the technical process.

The analytical instrument is gas chromatography (GC) with a thermal conductivity detector (TCD); the TCD is especially suitable for analysis of gas mixtures, and able to meet the requirements of peak height quantification in industrial analysis. The present invention is not intended to restrict the connection method and carrier gas settings of the GC apparatus.

Taking a low-pressure carburization process as an example, the amount of acetone contained in the acetylene can range from about 100 ppm to 10000 ppm or more. An acetylene stream supplied to the low-pressure carburization process has a flow rate ranging from about 0.5 $Nm^3/h$ to about 5 $Nm^3/h$ for each carburization chamber; the pressure in a carburization furnace is between 0 mbar and 20 mbar; and the operating temperature in the carburization furnace ranges from 850° C. to 1050° C., being 950° C. on average. The operating time of a low-pressure carburization processing procedure ranges from a few minutes to a few days for one batch, depending on the size and quantity of the components to be processed. Uninterrupted delivery of acetylene should be ensured in the low-pressure carburization processing procedure of one batch.

As shown in FIG. 1, in a double-branch acetylene gas supply apparatus, 10 and 20 respectively represent two acetylene cylinders, but could also be two sets of multiple cylinders. The two acetylene cylinders respectively output acetylene through a first branch and a second branch which converge to form a main pipeline.

V1 and V2 respectively represent pressure regulating valves arranged on the first branch and second branch, and can control pressure gauges or pressure transmitters PT1 and PT2, so as to adjust the pressure of acetylene outputted from the acetylene cylinder(s) 10 and/or 20 to a pressure required by operating conditions, to meet the requirement of an absolute pressure lower than 2.5 bar at the apparatus using acetylene.

V3 and V4 respectively represent control valves mounted on the two branches, may be solenoid valves, pneumatic valves or motorised valves, and are controlled by the data processing component. V5 is a control valve mounted on the main pipeline, may be a solenoid valve, pneumatic valve or motorised valve, and is also controlled by the data processing component. V3, V4 and V5 can control the two branches and the main pipeline to deliver feedstock to the analytical instrument in an acetylene content analysis apparatus.

30 is the acetylene content analysis apparatus, comprising the analytical instrument, the data processing component and the data transmission module.

V6 is a manual cut-off valve on the main pipeline; if control valve V3 or V4 fails, V6 can be opened or closed in a manual operation to guarantee system operation.

PT3 is a pressure gauge or pressure transmitter on the main pipeline, and indicates the pressure value of the acetylene stream to the apparatus using acetylene on the main pipeline.

FT1 is a flow rate controller on the main pipeline, and can be used to control the flow rate of output to the apparatus using acetylene.

After being outputted from the acetylene cylinder 10 or 20, the acetylene is adjusted to a suitable pressure via the pressure regulating valve V1 (or V2), and this pressure is displayed via the pressure gauge or pressure transmitter PT1 (or PT2) or transmitted to the acetylene content analysis apparatus. The acetylene then passes through the control valve V3 or V4 and reaches the control valve V5 of the main pipeline, and is then delivered to the analytical instrument in the acetylene content analysis apparatus 30. The analytical instrument may be mounted directly on the main pipeline, or may collect sample gas from the main pipeline for analysis. Results such as the solvent concentration obtained by gas chromatography (GC) analysis are sent to the data processing component by means of the data transmission module.

The data processing component performs logic judgement according to these results, and upon judging that the solvent concentration in the mixed gases outputted by the acetylene cylinder 10 is too high, correspondingly controls the open/closed state of V3, V4 and V5, to achieve switching of the acetylene cylinders or adjustment of the main pipeline and branch gas streams.

Embodiment 1

When acetylene cylinder 10 is open, V3 and V5 are in an open state, and V4 may be closed. If the acetone concentration in acetylene gas as measured by the analytical instrument is within a preset value range, the state in which acetylene cylinder 10 continuously outputs acetylene gas is maintained; if the acetone concentration in acetylene gas as measured by the analytical instrument exceeds a preset value, then V3 is closed, V4 and V5 are in an open state, and acetylene cylinder 20 opens, to start supplying acetylene gas. A person skilled in the art sets the preset value according to user demands, and the present invention does not impose restrictions in this respect; for example, it may be set to about 10000 ppm, or even 1000 ppm or even lower.

In addition, if the acetylene feedstock stream is interrupted due to a fault developing in acetylene cylinder 10 or for some other reason, acetylene cylinder 10 will also interrupt the gas supply and issue an alert, and a switch will take place automatically to having acetylene cylinder 20 supply acetylene.

Acetylene cylinder control and switching in various operating conditions can be achieved by means of this system.

The data processing component is connected by electronic communication to one or more of the following apparatus constituent parts, e.g. various types of pressure regulating valves, control valves, temperature sensors and level sensors in the acetylene cylinders, etc. The data processing component can control the gas temperature, pressure and weight in the acetylene cylinders, and can monitor the delivery pressure on the branches and the main pipeline, etc. For example, at a preset point monitored by the data processing component, when the cylinder weight and cylinder pressure of acetylene cylinder 10 clearly drop to below a preset value, the pressure regulating valves and control valves can be triggered automatically to switch to acetylene cylinder 20, in order to ensure that the acetylene gas stream in the subsequent technical process will not be interrupted.

When acetylene cylinder 10 is open, V3 and V5 are in an open state, and V4 may be closed. If the pressure value displayed by PT3 is lower than some set value despite the acetone concentration in acetylene gas as measured by the analytical instrument being within an expected range, the data processing component will control V4 and V5 to open and V3 to close so that acetylene cylinder 20 opens, and then check again whether the pressure value displayed by PT3 has returned to a compliant value.

In technical processes such as vacuum carburization, too high a solvent concentration in the acetylene might lead to soot or tar developing on the components, carbon deposits in the furnace, and blockage of the vacuum pump filter. The system and method of the present invention perform real-time monitoring of technical processes requiring continuous and steady delivery of acetylene at a high flow rate, and achieve automatic switching between acetylene cylinders according to real-time monitoring results. The system and method of the present invention can maximize the utilization of acetylene cylinders, saving manual and additional maintenance costs. The purity of acetylene gas is monitored more precisely, helping operators to gain an accurate understanding of the extent to which the amount of solvent in the cylinders is no longer suitable, and reducing the unnecessary number of times that the cylinders are switched and filled.

The above are merely preferred particular embodiments of the present invention, which are merely intended to illustrate the technical solution of the present invention without limiting the present invention. All technical solutions obtainable by those skilled in the art according to the concept of the present invention by logical analysis, reasoning or limited experiment should be included in the scope of the present invention.

What is claimed is:

1. A system for supplying acetylene to an apparatus that uses acetylene, comprising:
   at least one acetylene storage apparatus, for supplying a feedstock comprising acetylene and a solvent to an apparatus that uses acetylene; and
   an acetylene content analysis apparatus, comprising an analytical instrument and a data processing component;
   at least one pressure regulating valve is provided upstream of the apparatus using acetylene, for controlling the switching of each acetylene storage apparatus;
   wherein the analytical instrument comprises gas chromatography with a thermal conductivity detector or a flame ionization detector or Fourier-transform infrared spectroscopy, and is used to detect a solvent concentration in the feedstock;
   wherein the data processing component is configured to analyse the solvent concentration from the analytical instrument as time passes, compare the solvent concentration analysis with a preset value of solvent concentration, and output a control result; and
   wherein the control result outputted by the data processing component comprises the opening/closing of each pressure regulating valve.

2. The system according to claim 1, further comprising a data transmission module, for transmitting the solvent concentration from the analytical instrument to the data processing component.

3. The system according to claim 1, wherein the data processing component is a computer, a mobile device, or a logic controller with a microprocessor.

4. The system according to claim 1, wherein the solvent is selected from the group consisting of acetone, dimethylformamide, N-methylpyrrolidone, and a combination thereof.

5. The system according to claim 1, wherein the preset value of solvent concentration is 10000 ppm or less solvent contained in acetylene.

6. The system according to claim 1, wherein each acetylene storage apparatus outputs acetylene through a respective branch, and a control valve is further provided on each branch, for controlling each branch to deliver the feedstock to the acetylene content analysis apparatus.

7. The system according to claim 1, wherein the acetylene storage apparatus comprises a first acetylene storage apparatus and a second acetylene storage apparatus, and when the analytical instrument detects that the solvent concentration in an acetylene stream outputted by the first acetylene storage apparatus is higher than the preset value, a switch takes place to the second acetylene storage apparatus.

8. A method for supplying acetylene to an apparatus using acetylene, comprising:
 (1) providing at least one acetylene storage apparatus, for supplying a feedstock comprising acetylene and a solvent to the apparatus using acetylene;
 (2) arranging an acetylene content analysis apparatus, a pressure regulating valve and a control valve upstream of the apparatus using acetylene, the acetylene content analysis apparatus comprising an analytical instrument and a data processing component, the pressure regulating valve being used to control switching of each acetylene storage apparatus, and the control valve being used to control the delivery of the feedstock to the acetylene content analysis apparatus;
the analytical instrument detecting a solvent concentration in the feedstock and transmitting same to the data processing component, and the data processing component controlling the pressure regulating valve, to switch each acetylene storage apparatus.

* * * * *